United States Patent [19]

Dorschner

[11] 3,952,105

[45] Apr. 20, 1976

[54] ORGANOMETALLIC AGRICULTURAL FUNGICIDAL COMPOSITIONS AND METHODS FOR MAKING AND USING SAME

[75] Inventor: Kenneth P. Dorschner, Vienna, Va.

[73] Assignee: SCM Corporation, New York, N.Y.

[22] Filed: Mar. 27, 1972

[21] Appl. No.: 238,592

[52] U.S. Cl............................ 424/287; 424/288; 424/357
[51] Int. Cl.² .................... A01N 9/00; A01N 17/08
[58] Field of Search.................... 424/287, 288, 357

[56] References Cited
UNITED STATES PATENTS

| | | | |
|---|---|---|---|
| 3,062,637 | 11/1962 | Marples et al. ........................ 71/2.4 |
| 3,140,977 | 7/1964 | Duyjes et al. .................... 424/288 X |
| 3,334,119 | 8/1967 | Cohen................................. 260/429 |
| 3,342,581 | 9/1967 | Woodward et al. ..................... 71/65 |
| 3,431,288 | 3/1969 | Gibbons, Jr. et al. ............ 260/429.3 |
| 3,541,215 | 11/1970 | DeMarco et al.................... 424/287 |
| R26,639 | 8/1969 | Gibbons, Jr. et al. .............. 260/408 |

OTHER PUBLICATIONS

Gustav et al., C.A. Vol. 70 (1969) p. 4277p.
Deatley, C.A. Vol. 72 (1970) p. 65896c.

Primary Examiner—Sam Rosen
Assistant Examiner—Allen J. Robinson
Attorney, Agent, or Firm—Merton H. Douthitt; A. Joseph Gibbons

[57] ABSTRACT

Novel non-phytotoxic fungicidal compositions are described. They comprise a triorganostannoxy-substituted Group IVB metal ester, a neutral to alkaline clay and a minor proportion of anionic or nonionic surfactant. The compositions are prepared by intimately blending the ingredients. At least a portion of the surfaces of growing plants are contacted with the compositions of this invention to control pathogenic mircroorganisms without injuring the protected plant.

8 Claims, No Drawings

ORGANOMETALLIC AGRICULTURAL FUNGICIDAL COMPOSITIONS AND METHODS FOR MAKING AND USING SAME

BACKGROUND OF THE INVENTION

This invention relates to substantially non-phytotoxic fungicidal compositions and more particularly those containing a fungicidally active material, a triorganostannoxy-substituted ester of a Group IVB metal such as titanium.

Numerous fungicides have been prepared including the triorganostannoxy-substituted Group IVB metal esters which are disclosed in U.S. Pat. Nos. 3,334,119; 3,541,215; 3,431,288; and U.S. Re. No. 26,339 of U.S. Pat. No. 3,361,775. Upon contact with a plant such esters are noticeably phytotoxic, and this limits their practical use to protect the foliage, stems, and other exposed portions of crops and growing plants from fungal attack.

The closest art known to the applicant is set forth in Form 1082, attached hereto.

BRIEF SUMMARY OF THE INVENTION

It has now been discovered that such fungicidally active esters can be converted by the practice of this invention into an essentially non-phytotoxic composition useful to protect plants from pathogenic fungi attack. The present improvement comprises an intimate mixture of said triorganostannoxy-substituted Group IVB metal ester with finely divided neutral to alkaline clay in the proportion of about 1 to about 4 parts of said ester per part of said clay. Surprisingly these neutral to alkaline clay-ester mixtures quite rich in such phytotoxic fungicidal ingredient have been found to be less damaging to a wide variety of growing plants than a corresponding mixture relatively lean in such phytotoxic fungicidal ingredient when the same total amount of active ingredient is applied per acre. Hence, the selection of the type of and restriction of the proportion of the clay are especially unobvious features of this invention.

Another aspect of this invention is a composition which comprises an intimate mixture of the said ester with finely divided neutral to alkaline clay wherein said mixture is combined with a nonionic or anionic surfactant in minor proportion to provide a wettable powder. Such compositions are advantageous in providing prolonged fungicidal protection to the plants to which they are applied while yet possessing an unusually low phytotoxicity. In addition, they are relatively inexpensive and stable.

Another aspect of this invention is an improved process for producing a fungicidally active non-phytotoxic composition which comprises intimately blending said ester with finely divided neutral to alkaline clay in the proportion of about 1 to 4 parts of said ester per part of said clay and a minor proportion of an anionic or nonionic surfactant.

Another aspect of the present invention is a process for protecting plants from pathogenic fungi which comprises depositing on their foliage the above-described non-phytotoxic composition. Valuable plants can be protected by spraying the foliage directly with the said composition, usually in the form of a wettable powder dispersed in a water vehicle.

DETAILED DESCRIPTION OF THE INVENTION

The tin-containing substituent in the above Group IVB ester can be represented as the triorganotin radical $R_3Sn$. The organic groups on such tin ordinarily will be the same or different aryl or alkyl but they can be alkenyl, cycloalkyl, aralkyl, alkaryl, or alkenylaryl as shown in the above-cited U.S. patents.

The Group IVB metal ester moiety of the compound can be of several convenient types as shown in U.S. Pat. No. 3,541,215 and U.S. Re. No. 26,639 of U.S. Pat. No. 3,361,775, particularly the formula:

where M is a Group IVB metal and R' represents the same or different alkyl or alkenyl groups having 1–18 carbon atoms.

Alternatively, such Group IVB metal ester moiety of the compound can result from three of the Group IVB metal valences being satisfied by the residue of the trialkanolamine, more particularly in accordance with the formula:

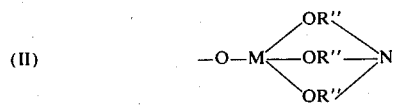

where M is a Group IVB metal and R'' is an alkylene radical of 2 to 3 carbon atoms as is shown in U.S. Pat. No. 3,334,119.

Additionally, the Group IVB metal ester moiety of the molecule can be displaced from the triorganotin substituent by a disubstituted metaloxy group of two of them, also as set forth in U.S. Pat. No. 3,334,119, that is in accordance with the formula:

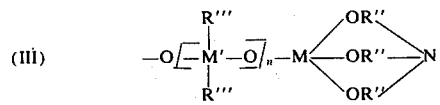

wherein R'' and M have the same significance as set forth in the previous paragraph and where M' is tin, titanium, silicon, zirconium, or hafnium, the R''' groups are the same or different hydrocarbyl groups such as alkyl, aryl, and alkenyl, or hydrocarbyloxyl such as alkoxy, and "n" is an integer of 1 or 2.

Such triorganostannoxy-substituted Group IVB metal esters wherein the ester of Formula I, above, is reacted with diethanolamine to form predominantly polymeric esters according to U.S. Pat. No. 3,431,288, also has utility for the purposes of this invention.

In representative organotin moieties ($R_3Sn—O—$) of the mildewicidally effective compound, the R radicals can be alkyl, alkenyl, cycloalkyl, and the like. Thus, when $R_3$ is trialkyl, it can represent trimethyl, triethyl, tripropyl, tri-i-propyl, tributyl, tripentyl, tri-n-hexyl, tri-2-ethylhexyl, trioctyl, trinonyl, and unsymmetrical groups such as diethyloctyl, diethylhexyl, dipropylhexyl, and the like. When $R_3$ is trialkenyl, it can represent trivinyl, triallyl, triisopropenyl, which are the most readily available commercial types. Tricyclohexyl and tricyclopentyl are preferred when $R_3$ is tricycloalkyl. The tributyl group is generally preferred because it is readily available commercially as the oxide or acetate and it is generally recognized that combinations of alkyl groups totalling 12 carbon atoms provide desirable fungicidal action in certain use requirements.

Similarly, when $R_3$ in such organotin moiety is triaryl it can represent, for example, triphenyl, trimethylphenyl, triethylphenyl, trinaphthyl, tribenzyl, triphenylethyl, tri-p-vinylphenyl, and the like. The triphenyltin group is usually preferred both because of its effectiveness and low phytotoxicity in the composition, and also because it is readily available commercially or can be synthesized from commercially available tetraphenyltin. Additionally, such R radicals can be further represented by mixed alkyl or alkenyl and aryl types, for example, vinyldiphenyl, dibenzylethyl, divinylcyclohexyl and diethylstyrl groups which are advantageous when extra reactivity is desired.

In the triorganostannoxy derivative of esters of Formula I above, M represents a Group IVB metal; i.e., hafnium, titanium, and zirconium. Generally used esters are those of titanium and zirconium because of their commercial availability, and especially preferred is titanium because the lower alkyl esters are readily purified by vacuum distillation. The R' groups of Formula I can be alkyl, alkenyl, or fluoralkyl groups having 1–18 carbon atoms and may be the same or different. Generally preferred R' groups are lower alkyl groups such as propyl, isopropyl, and butyl because these metal esters are commercially available and can be readily purified by vacuum distillation.

In the triorganostannoxy derivatives of esters of Formula II above, the R'' groups usually consist of alkylene groups of 2–3 carbon atoms. Preferred groups are ethylene and methylethylene. M in Formula II has the same significance as described above, and titanium is preferred.

In the triorganostannoxy derivatives of esters of Formula III, M and R'' have the same significance as set forth above, and M' is represented by tin, titanium, silicon, zirconium, or hafnium; and the R''' groups are the same or different hydrocarbyl groups such alkyl, aryl, and alkenyl or hydrocarbyloxyl groups such as alkoxy, and "n" is an integer of 1 or 2. Preferred groups shown within the bracket are dibutylstannoxy or diethylsiloxy groups, but alkoxy titaniumoxy groups may be used.

Clays have been commonly used as convenient and inexpensive inert carriers for fungicides. The clays which are advantageous in this invention can be either synthetic or natural clays which exhibit pH ranges from about 7.0 to about 8.5. pH of clay is usually determined by suspending the clay in water of pH 7.0 and reading the pH using a commercial pH meter. Common types which may fit into this classification are the diatomaceous earth, the micas, vermiculites, talcs, and some basic types of montmorillonoids. Particularly preferred are the attapulgite group of clays and especially suitable for the formulations of wettable powders and dust concentrates is Attaclay with a particle size range of about 5 to about 50 microns. Attaclay is an attapulgite type clay usually mined in Georgia or Florida by Minerals & Chemicals Corporation of America and possesses the following typical average chemical analysis: $SiO_2$, 67.0%; $Al_2O_3$, 12.5%; MgO, 11.0%; $Fe_2O_3$, 4.10%; CaO, 2.5%; other, 3.0%. It is non-abrasive and has a specific gravity of 2.3–2.6 and a pH of 7.5 to 8.0. In its preferred form it has a particle size range of 1–50 microns; the major portion of the particles usually is below 30 microns in size. It has excellent wettability. Especially preferred are formulations made with Attaclay and water previously brought to a pH of 8.5. Acid clays of the type derived from fuller's earth, bentonite, and the like are to be avoided.

Anionic surfactants which can be employed in processes of this invention include metal salts of fatty acids, such as, for example, alkali metal and alkaline earth metal salts of naturally occurring fatty acids; e.g., stearic, palmitic, oleic, lauric, myristic, arachidic, etc., which are commonly referred to as soaps and amino compounds of such fatty acids. Turkey red oil, sulfonated alcohols, fatty alcohol sulfates, sulfonaphthanates, petroleum sulfonates, aromatic sulfonates; e.g., sulfonated alkyl naphthalene; alkyl sulfosuccinic esters, aryl alkyl sulfonic acids, sulfonated amides, sulfonated phenols, and other sulfonated, phosphated, or borated compounds corresponding to the foregoing can also be employed.

Other anionic surfactants include alkali metal salts of: sulfonated ricinoleic acid, tetrahydronaphthalene sulfonic acid, propyl and butyl naphthalene sulfonic acid, butyl ricinoleic acid sulfonate, sulfuric acid esters of alcohols from coconut oil; sulfonated fatty acid ethanol amides, polybutyl naphthalene sulfonic acid, heptadecyl benzene sulfonic acid, secondary alcohol sulfonic acids, dioctyl sulfosuccinic acid, condensation products of fatty acids and diethanolamine, alkyl benzene sulfonic acids, alkyl sulfonic acids, and the like.

Specifically, advantageous anionic surfactants which may be employed are the long-chain acid esters of sodium isethionate. The oleic acid of sodium isethionate is especially preferred. This compound is known commercially by the trade name of Igepon AP-78.

Nonionic surfactants which can be employed in processes of this invention include, but are not limited to, polyoxyethylene surfactants, polyoxyethylene esters of fatty, rosin, and tall oil acids, fatty acid esters of sorbitan, especially the monolaurate, monooleate, and the monostearate. "Tween 20" is a polyoxyalkylene derivative of sorbitan monolaurate. Equally advantageous for the purposes of this invention are the glycol esters of fatty acids, such as ethylene glycol stearate, and diethylene glycol monostearate. Other specific surfactants include a polymerized oxyethylcondensate sold under the name of Igepal CA, a trademark of General Dyestuff Corporation, and condensation products of ethylene oxide with a partial fatty acid ester of hexitol anhydrides derived from sorbitol and sold under the trademarks, "Tween 60", "Tween 80", and "Tween 81" by the Atlas Powder Company. In addition, mixtures of anionic and nonionic surfactants can be used for purposes of this invention. Any of the foregoing surfactants may be employed in the conventional manner.

When higher than 80 weight percent of the fungicidal ester is used in the clay formulation, the nonphytotoxic character tends to be lost. Similarly when lower than 50 weight percent of the fungicidal ester is used, the phytotoxicity also increases. Hence, selection of the type of and restriction of the proportion of the clay are specially unobvious features of this invention.

Although these compositions were tested mainly as foliar fungicides to be applied as aqueous or oil emulsion sprays, they can also be used to treat soil and can be applied as dust fumigants.

The following examples are intended to illustrate the invention but not to limit the scope thereof, parts and percentages being by weight unless otherwise specified.

EXAMPLE 1

The following wettable powder formulations, using the compounds and amounts listed below, were prepared by intimately mixing together in a ribbon blender triphenylstannoxytitanium triethanolamine (hereinafter referred to as TPSTEA), the clay, and the surfactant.

| Composition | TPSTEA | Attaclay | Pikes Peak Clay | Igepon AP-78 |
|---|---|---|---|---|
| 1 | 60 | 38 | 0 | 2 |
| 2 | 30 | 67 | 0 | 3 |
| 3 | 15 | 81 | 0 | 4 |
| 4 | 60 | 0 | 38 | 2 |
| 5 | 30 | 0 | 67 | 3 |
| 6 | 15 | 0 | 81 | 4 |

Components Weight Percent

The Attaclay formulations of compositions 1, 2, and 3 were prepared using water previously brought to a pH of 8.5 by addition of aqueous sodium hydroxide. The acidic Pikes Peak Clay, compositions 4, 5, and 6 were formulated in water at pH 5.5.

Attaclay, a hydrated magnesium aluminum silicate of specific gravity 2.3–2.6, has an average particle size of 1.2 microns and pH 7.5 to 8.0. Acidic Pikes Peak Clay, a montmorillonite clay produced in Pikes Peak, Georgia, by General Reduction Company, exhibits pH about 5.0 in water. It has a particle size such that 98 percent will pass through a 100 mesh screen (USS).

Triphenylstannoxytitanium triethanolamine and oleic acid ester of sodium isethionate (Igepon AP-78) were used in each formulation and the amount and type of clay was varied. A control fungicidal formulation was prepared by suspending the same organometallic compound in a 50/50 by volume mixture of acetone and water using 0.05 percent by weight of Tween-20 (polyoxyethylene derivative of sorbitan monolaurate) based on weight of total composition.

EXAMPLE 2

Seedling plants, as shown in the following tables, were given post-emergent foliar treatment by applying the formulations listed in Example 1 in a manner to deposit an equivalent of 8 pounds active organometallic ingredient per acre on a broadcast basis. The plants were maintained under ambient greenhouse conditions and were observed at 24 hours and at 120 hours after treatment for phytotoxic responses. This allowed observations on rate and extent of possible plant injury. The 24-hour response is shown in Table I, and the 5-day response is shown in Table II. Corresponding phytotoxicity ratings are given in Tables III and IV. The values given in Tables III and IV account for percent kills and are adjusted to include reductions in plant health and vigor; a phytotoxicity rating of 0 indicates no chemical injury, while a rating of 100 indicates death of the plant. The total of points for each species allows a ready comparison of the efficiency of each formulation. Thus, in Table IV, wettable powder formulations of triphenylstannoxytitanium triethanolamine with 38 percent Attaclay shows a phytotoxicity rating of 60, as opposed to a rating of 160 when an acidic clay is used, and as opposed to a rating of 656 when the same quantity is dispersed in an acetone/water formulation without clay. It is noted that a basic clay formulation is more deisrable than an acidic clay formulation and that the actual proportion of clay to triphenylstannoxytitanium triethanolamine is equally important and critical to optimum protection of the crop. All treatments gave full fungicidal protection to the crops.

TABLE I

24-HOUR RESPONSE OF TEST PLANT SPECIES TO POST EMERGENCE FOLIAR TREATMENT[a]
VIGOR RATING[b]

| Composition | Mustard | Soybean | Coffeeweed | Pigweed | Corn | Crabgrass | Cotton | Barnyard Grass |
|---|---|---|---|---|---|---|---|---|
| 1 | 4 | 4 | 5 | 5 | 5 | 5 | 5 | 5 |
| 2 | 3 | 4 | 5 | 4 | 5 | 5 | 5 | 5 |
| 3 | 2 | 3 | 5 | 2 | 4 | 4 | 5 | 4 |
| 4 | 3 | 4 | 5 | 3 | 5 | 5 | 5 | 5 |
| 5 | 2 | 3 | 5 | 2 | 4 | 4 | 4 | 5 |
| 6 | 1 | 2 | 4 | 1 | 4 | 3 | 4 | 4 |
| Control[c] | 1 | 1 | 2 | 1 | 2 | 2 | 3 | 1 |

[a]No plants were killed in 24 hours
[b]Vigor Ratings:
  1 - Severe Injury - Plants will eventually die
  2 - Moderate Injury - Plants may or may not recover
  3 - Moderate Injury - Plants will recover
  4 - Slight Injury - Plants only slightly behind untreated control
  5 - No Injury - Plants similar to untreated control
[c]Active organometallic dispersed in acetone/water (50/50 volume percent) plus .05% by weight Tween-20

TABLE II

5-DAY RESPONSE OF TEST PLANT SPECIES TO POST-EMERGENCE FOLIAR TREATMENT

| Composition | Mustard Vigor | %Kill[a] | Soybean Vigor | %Kill | Coffeeweed Vigor | %Kill | Pigweed Vigor | %Kill | Corn Vigor | %Kill | Crabgrass Vigor | %Kill | Cotton Vigor | %Kill | Barnyard Grass Vigor | %Kill |
|---|---|---|---|---|---|---|---|---|---|---|---|---|---|---|---|---|
| 1 | 3 | 0 | 5 | 0 | 5 | 0 | 4 | 0 | 4 | 0 | 5 | 0 | 4 | 0 | 5 | 0 |
| 2 | 2 | 90 | 3 | 0 | 4 | 0 | 3 | 0 | 4 | 0 | 5 | 0 | 3 | 0 | 4 | 0 |
| 3 | 1 | 95 | 3 | 0 | 3 | 0 | 3 | 80 | 4 | 0 | 4 | 0 | 2 | 60 | 4 | 0 |
| 4 | 2 | 50 | 4 | 0 | 4 | 0 | 3 | 0 | 4 | 0 | 4 | 0 | 4 | 0 | 5 | 0 |
| 5 | 2 | 90 | 3 | 0 | 3 | 0 | 3 | 10 | 4 | 0 | 4 | 0 | 3 | 0 | 4 | 0 |
| 6 | 1 | 95 | 2 | 0 | 2 | 0 | 2 | 80 | 3 | 0 | 3 | 0 | 2 | 60 | 4 | 0 |
| Control[c] | 1 | 95 | 1 | 10 | 1 | 95 | 2 | 95 | 1 | 80 | 2 | 20 | 1 | 75 | 3 | 25 |

[a]Percent Kill - indicates the percentage of the original plants not surviving at the end of the 5-day period.
[b]Vigor Ratings:
  1 - Severe Injury - Plants will eventually die
  2 - Moderate Injury - Plants may or may not recover

TABLE II-continued

5-DAY RESPONSE OF TEST PLANT SPECIES TO POST-EMERGENCE FOLIAR TREATMENT

| Composition | Mustard Vigor | %Kill[a] | Soybean Vigor | %Kill | Coffeeweed Vigor | %Kill | Pigweed Vigor | %Kill | Corn Vigor | %Kill | Crabgrass Vigor | %Kill | Cotton Vigor | %Kill | Barnyard Grass Vigor | %Kill |
|---|---|---|---|---|---|---|---|---|---|---|---|---|---|---|---|---|

3 - Moderate Injury - Plants will recover
4 - Slight Injury - Plants only slightly behind untreated control
5 - No Injury - Plants similar to untreated control

[c]Active organometallic dispersed in acetone/water (50/50 by volume percent) plus .05% by weight Tween-20

TABLE III

24-Hour Phytotoxicity Ratings[a] of Post-Emergence Foliar Treatment

| Test Plant Species | Acetone/Water[c] Only | Attaclay Wettable Powders (Basic) | | | Pikes Peak Wettable Powders (Acidic) | | |
|---|---|---|---|---|---|---|---|
| | | 38% | 67% | 81%[b] | 38% | 67% | 81% |
| Mustard | 60 | 10 | 30 | 60 | 30 | 60 | 60 |
| Soybean | 60 | 10 | 10 | 30 | 10 | 30 | 60 |
| Coffeeweed | 60 | 0 | 0 | 0 | 0 | 0 | 10 |
| Pigweed | 60 | 0 | 10 | 60 | 30 | 60 | 60 |
| Sweet Corn | 60 | 0 | 0 | 10 | 0 | 10 | 10 |
| Crabgrass | 60 | 0 | 0 | 10 | 0 | 10 | 30 |
| Cotton | 30 | 0 | 0 | 0 | 0 | 10 | 10 |
| Barnyard Grass | 60 | 0 | 0 | 10 | 0 | 0 | 10 |
| Totals | 450 | 20 | 50 | 180 | 70 | 180 | 250 |

A rating of 0 indicates no chemical injury, while a rating of 100 indicates death of the plant.
[a]Data extracted from Table I and adjusted to relect vigor ratings numerically as follows:

| Vigor Rating | % Kill Adjusted to Include |
|---|---|
| 5 | % Kill Only |
| 4 | % Kill plus 10% of remainder |
| 3 | % Kill plus 30% of remainder |
| 1 and 2 | % Kill plus 60% of remainder |

[b]Indicates amounts of clay in original formulation
[c]Active organometallic dispersed in acetone/water (50/50 by volume percent) plus .05% by weight Tween-20

TABLE IV

5-Day Phytotoxicity Ratings[a] of Post-Emergence Foliar Treatment

| Test Plant Species | Acetone/Water[c] Only | Attaclay Wettable Powders (Basic) | | | Piles Peak Wettable Powders (Acidic) | | |
|---|---|---|---|---|---|---|---|
| | | 38% | 67% | 81%[b] | 38% | 67% | 81% |
| Mustard | 98 | 30 | 96 | 98 | 80 | 96 | 98 |
| Soybean | 64 | 0 | 30 | 30 | 10 | 30 | 60 |
| Coffeeweed | 98 | 0 | 10 | 30 | 10 | 30 | 60 |
| Pigweed | 98 | 10 | 30 | 86 | 30 | 37 | 92 |
| Sweet Corn | 92 | 10 | 10 | 10 | 10 | 10 | 30 |
| Crabgrass | 68 | 0 | 0 | 10 | 10 | 10 | 30 |
| Cotton | 90 | 10 | 30 | 84 | 10 | 30 | 84 |
| Barnyard Grass | 48 | 0 | 10 | 10 | 0 | 10 | 10 |
| Totals | 656 | 60 | 216 | 358 | 160 | 253 | 464 |

A rating of 0 indicates no chemical injury, while a rating of 100 indicates death of the plant.
[a]Data extracted from Table II and adjusted to reflect vigor ratings numerically as follows:

| Vigor Rating | % Kill Adjusted to Include |
|---|---|
| 5 | % Kill Only |
| 4 | % Kill plug 10% of remainder |
| 3 | % Kill plus 30% of remainder |
| 1 and 2 | % Kill plus 60% of remainder |

[b]Indicates amounts of clay in original formulation. Compare Example I for compositions.
[c]Active organometallic dispersed in acetone/water (50/50 by volume percent) plus .05% by weight Tween-20

What is claimed is:

1. In a fungicidal composition having a fungicidally active but phytotoxic triorganostannoxy-substituted ester of a Group IVB metal, the improvement rendering said ester essentially nonphytotoxic which comprises:
an intimate mixture of said ester with finely divided neutral to alkaline clay in the proportion of about one to four parts of said ester per part of said clay.

2. The composition of claim 1 wherein said mixture is combined with a surfactant in minor proportion to provide a wettable powder, said surfactant being nonionic, anionic, or a mixture of the same.

3. The composition of claim 2 wherein said ester is a triarylstannoxy-substituted trialkanolamine titanate.

4. The composition of claim 2 wherein said ester is a tri (lower alkyl) stannoxy-substituted trialkanolamine titanate.

5. The composition of claim 2 where said ester is triphenylstannoxy triethanolamine titanate.

6. The composition of claim 2 wherein said clay is an attapulgus clay.

7. The composition of claim 2 wherein said surfactant is anionic.

8. A non-phytotoxic fungicidal composition comprising 1 to 4 parts of a triorganostannoxy Group IVB metal ester admixed with 1 part of a finely divided clay having a pH from about 7.0 to about 8.5.

* * * * *